(12) United States Patent
Covannon et al.

(10) Patent No.: US 7,384,146 B2
(45) Date of Patent: Jun. 10, 2008

(54) HEALTH CARE KIOSK HAVING AUTOMATED DIAGNOSTIC EYE EXAMINATION AND A FULFILLMENT REMEDY BASED THEREON

(75) Inventors: Edward Covannon, Ontario, NY (US); Elena A. Fedorovskaya, Pittsford, NY (US); Dana W. Wolcott, Honeoye Falls, NY (US); Serguei Endrikhovski, Rochester, NY (US); Michael A. Marcus, Honeoye Falls, NY (US)

(73) Assignee: Carestream Health, Inc., Rochester, NY (US)

( * ) Notice: Subject to any disclaimer, the term of this patent is extended or adjusted under 35 U.S.C. 154(b) by 171 days.

(21) Appl. No.: 11/168,043

(22) Filed: Jun. 28, 2005

(65) Prior Publication Data

US 2006/0290885 A1 Dec. 28, 2006

(51) Int. Cl.
*A61B 3/02* (2006.01)
*A61B 3/14* (2006.01)
(52) U.S. Cl. ..................... 351/223; 351/206
(58) Field of Classification Search ............... 351/223
See application file for complete search history.

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,469,261 A | 11/1995 | Hellmuth et al. | |
| 5,491,524 A | 2/1996 | Hellmuth et al. | |
| 5,493,109 A | 2/1996 | Wei et al. | |
| 5,537,162 A | 7/1996 | Hellmuth et al. | |
| 6,293,674 B1 | 9/2001 | Huang et al. | |
| 6,540,355 B1* | 4/2003 | Couture | 351/203 |
| 6,682,195 B2 | 1/2004 | Dreber | |
| 6,704,588 B2 | 3/2004 | Ansari et al. | |
| 6,761,454 B2 | 7/2004 | Lai et al. | |
| 2001/0025226 A1* | 9/2001 | Lavery | 702/108 |
| 2002/0091321 A1 | 7/2002 | Goldstein et al. | |
| 2002/0182152 A1 | 12/2002 | Goldstein et al. | |
| 2006/0023163 A1* | 2/2006 | Foster | 351/246 |

OTHER PUBLICATIONS

A. Fercher; "Optical Coherence Tomography" Journal of Biomedical Optics; Apr. 1996. vol. 1, No. 2, pp. 157-173.
L. Ventura et al.; "Automatic diagnostic system for measuring ocular refractive errors" SPIE, vol. 2673, pp. 243-251.
L. Clare et al.; "Relearning Face-Name Associations in Early Alzheimer's Disease" Neuropsychology 2002, vol. 16, No. 4, pp. 538-547.

(Continued)

*Primary Examiner*—Jordan M. Schwartz
*Assistant Examiner*—James C Jones

(57) ABSTRACT

A stand-alone station such as a kiosk (10) includes automated equipment for performing eye examination procedures on a user positioned in the station (11). Information derived from the examination determines possible existence of a correctable medical condition. The station includes a user interface (22) and a fulfillment remedy section (30) that addresses the medical condition, as by fabrication of eyeglasses (32) for correction of refraction error, or by communicating treatments through the user interface to the user for treating such conditions as age-related macula degeneration, Alzheimer's disease, or visual field impairment. The station also includes a payment device (24) allowing the user to directly pay for the procedure and to indirectly pay using identified health insurance coverage.

12 Claims, 7 Drawing Sheets

OTHER PUBLICATIONS

E. Kasten et al.; "Computer-Based Training of Stimulus Detection Improves Color and Simple Pattern Recognition in the Defective Field of Hemianopic Subjects" Journal of Cognitive Neuroscience, vol. 12, No. 6; pp. 1001-1012.

Photodynamic Therapy of Subfoveal Choroidal Neovascularization in Age-related Macular Degeneration With Verteporfin; Arch Ophthalmology, vol. 117, Oct. 1999, pp. 1329-1345.

* cited by examiner

HEALTH CARE KIOSK HAVING AUTOMATED DIAGNOSTIC EYE EXAMINATION AND A FULFILLMENT REMEDY BASED THEREON

FIELD OF THE INVENTION

The present invention is directed to the field of user-operated medical diagnostic and remedy dispensing kiosks.

BACKGROUND OF THE INVENTION

Currently, in the case of a health problem a patient goes to the medical specialist where the patient undergoes a series of tests in order to formulate a diagnosis, based on which a treatment can be prescribed. Often the patient has to go through several visits to different specialists and then to the place where the treatment could be delivered. Acquiring eyewear to correct the problem of vision loss is an example of the current standard health care practice. Although such practice provides a high quality solution for the common health care problems, it has several limitations and shortcomings. Among them are cost, duration of time before the problem is detected and corrected, and inapplicability for the counties where the health care systems are not well established and operated, and are lacking well-trained specialists. The latter is especially obvious in developing nations where the shortage of health care specialists, funding, and equipment results in serious problems for the population's health. To overcome those shortcomings systems are being developed that can perform several steps related to testing or diagnostics in an automatic fashion. In the area of optometry, for example, there exist several devices that perform automatic measurement of the refractive errors. These devices are known as Autorefractometers. For example, the Auto Refractometer Model KA-1000, manufactured by Kowa Optimed Inc., Torrance, Calif., which is an ophthalmic products division of Kowa Company, Japan, is used to automatically specify a corrective prescription of glasses or contact lenses for a user. Another device, Luneau L62-3D, manufactured by LUNEAU S.A., France, in addition to measuring refractive errors of the lens, provides an estimation of the optical properties and topography of cornea, which is particularly useful for a proper contact lens prescription. The systems, which perform higher order aberration measurements employing a wave front sensor, are currently being sold and further developed. Such a device is being developed by Ophthonix, Inc., San Diego, Calif. The Ophthonix device is described in U.S. Pat. No. 6,761,454 and it shines light into the eye and measures changes in the wave properties of the light reflected back by the retina. From these changes, the apparatus can calculate the measurements on any existing irregularities of the eye lens.

Automatic measurement of refractive errors or higher order aberrations enables performance of necessary diagnostics of the person's vision in terms of the prescription lenses. Devices of this type can be operated by an assistant who requires only a limited training or by the user. However, such devices are not capable of automatically producing corrective eyewear, which is a highly desirable attribute for countries line China and India, where a large percentage of the population with the near- or far-sightedness lacks an access to the prescription eyewear.

In order to provide prescription eye-ware, presently an optometrist or an eye professional performs a variety of measurements including bridge size, inter-pupillary distance, temple length, eye size and visual axis measurements, in addition to the measurements of refractive errors and/or higher order aberrations, which could be done automatically as described above. Usually, the optometrist performs a process of fitting the eyewear to the person's head, which may be time consuming. This operation is done to properly adjust the frame to the person's facial structure.

U.S. Pat. No. 6,682,195 discloses a method of measuring parameters required for fitting of an eyeglasses frame using digital cameras. Examination of the eye is not only used for prescribing corrective eyewear, but can be also used for screening and diagnosing a variety of ophthalmologic diseases, such as cataract, uveitis, glaucoma, macula degeneration, visual field changes and others.

High resolution longitudinal and depth imaging can be performed by optical coherence tomography (OCT) as described in articles "Optical Coherence Tomography" by D. Huang et al., Science 254, (1991), pp. 1178-1181; and "Optical Coherence Tomography" by A. F. Fercher, in Journal of Biomedical Optics Vol. 1, No. 2, April 1996, pp. 157-173. An OCT based instrument called StratusOCT is now commercially available from Carl Zeiss Meditec, Jena, Germany which produces OCT cross sectional images of the retina for objective measurement and clinical evaluation for the detection of glaucoma and retinal diseases. Examples of OCT apparatus for longitudinal and transverse imaging are described in U.S. Pat. Nos. 5,493,109; 5,537,162; 5,491,524; 5,469,261; 5,321,501; and 5,459,570. Another example, U.S. Pat. No. 6,293,674 discloses the use of optical coherence tomography (OCT) system for diagnosing glaucoma while examining the eye. This patent describes an apparatus that images the patient's retina to determine the parameters of the retinal nerve fiber layer, such as thickness, relevant to glaucoma.

It is also known that eye exams may lead to detecting other illnesses. Alzheimer's disease, mental disorders, diabetes, cancer and drug usage were found to generate changes in the eye and eye behavior. For example, in the U.S. Patent Application Publication Ser. No. 2002/0182152 A1 described a method of diagnosing Alzheimer's disease by applying a dynamic light scattering probe to the eye lens of the mammals. In research studies it was found that the beta amyloid proteins that form plague in the brain in Alzheimer's patients tend to aggregate in the eye lens which increases the light scattering characteristics of the lens and can be therefore detected at the early stage of the illness.

U.S. Pat. No. 6,704,588 discloses a method and an apparatus for non-invasive determination of blood glucose levels by performing measurements in the eye using light polarization effects.

The above systems provide measurements related to the condition of the eye with respect to a number of illnesses and health status but do not provide any automated means of fulfillment.

There is therefore a need for systems that will provide automated diagnosis of medical conditions, related to vision, ophthalmologic diseases as well as other types of health conditions, and that will automatically provide the necessary fulfillment of the patient's needs as dictated by the automated diagnosis. The present invention satisfies this need.

The foregoing and other objects, features, and advantages of the invention will be apparent from the following more particular description of the preferred embodiments of the invention, as illustrated in the accompanying drawings.

SUMMARY OF THE INVENTION

In accordance with the invention there is provided a health care kiosk, which is adapted to diagnose a medical condition of a user based on an examination of the user's eyes and to provide a remedy therefor. The health care kiosk comprises a user accommodation section adapted to locate a user in at least one position that enables an interaction between the station and the user, and a user interface that is adapted to permit a user to input data relevant to the user. The kiosk also includes an eye examination and information processing section adapted to examine at least one of a user's eyes while the user is in the at least one position, wherein the at least one position enables the user to align their eyes with an input to the eye examination section. The eye examination section is adapted to examine the eyes and to provide from the examination at least one of first information relevant to a state of the user's eyes and second, diagnostic, information based on the first information that is indicative of a medical condition of the user. Finally, the kiosk includes a fulfillment section adapted to respond to information from the examination section to provide a fulfillment remedy pertinent to the state of the eyes or other diagnosed medical condition.

BRIEF DESCRIPTION OF THE DRAWINGS

In the detailed description of the preferred embodiments of the invention presented below, reference is made to the accompanying drawings, in which.

DETAILED DESCRIPTION OF THE INVENTION

Figure 1:
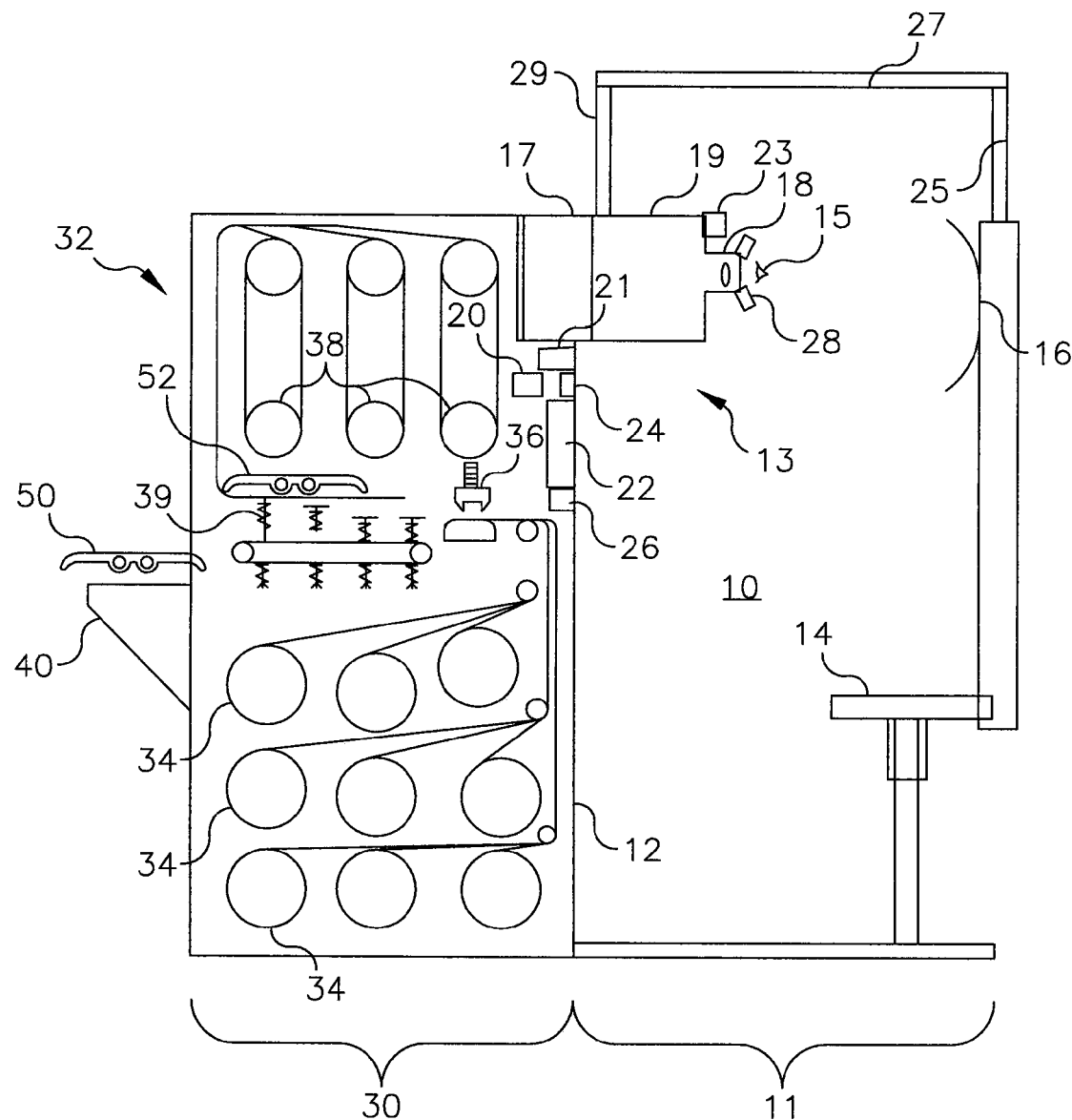
FIG. 1 is a side schematic view of a health care kiosk in which eyeglasses with corrective lens are dispensed in accordance with the present invention.

Turning now to FIG. 1, there is shown a health care kiosk 10 which comprises a stand-alone digital imaging device adapted to diagnose a medical condition of a user based on an examination of the user's eyes and to provide a remedy therefor, in accordance with one preferred embodiment of the invention. In particular, this kiosk is preferably an optometric kiosk, adapted to perform an eye-sight examination and to administer an issuance of corrective eye-ware specific to a person's needs. The illustrated kiosk includes a user accommodation section 11, having a user's seat 14, adapted to locate a user in at least one position that enables an interaction between the station and the user, a user interface device 22 through which a user can initiate the process of optometric service. This user interface section further includes a user identification and ID validation module 21, and a mechanism for payment 24, for example by means of a credit card. The user interface device 22 also permits the user to provide or insert relevant data about the user, such as for example medical history. The illustrated kiosk further includes an enclosure 12, having an eye examination section 13 adapted to examine a user's eyes while the user is positioned on the seat. The eye examination and information processing section 13 includes an eye examination module 19, an eyepiece 18, an information processor 17, and a detachable alignment fixture 28. The seat 14 is preferably height adjustable and preferably includes a head rest 16. In order to enable the user to align his or her eyes 15 with an input eyepiece 18 a detachable alignment fixture 28 is provided. This detachable alignment fixture 28 ensures the proper position of the user's eyes and allows the proper hygiene to be provided. It can either be cleaned between different users or it can be a single-use item. The eyepiece 18 can be adapted for use with one or two eyes. Eye examination module 19 includes a test device or suite of test devices adapted to perform eye examinations to determine the health condition of the user. In the illustrated embodiment, the eye examination module 19 preferably comprises a refractometer and/or wave front sensor, as described above, designed to measure refractive errors or higher order aberrations in the eye for producing corrective eyewear. The data from eye examination module 19 is collected and processed by information processor 17.

Although the aforementioned devices such as refractometers or wave front sensors imply a limited participation of an assistant or a device operator, other, fully automatic systems, have also been proposed and can be utilized in the invention. One such system is described by Ventura et al. in "Automatic diagnostic system for measuring ocular refractive errors," SPIE, Vol. 2673, pp. 243-251. The information processor 17 is operative in response to the output of the eye examination module 19 to generate information relevant to the state of the user's eyes, in this case prescription data for eyeglasses to correct for refractive errors or higher order aberrations of the eyes uncovered in the examination.

Alternatively, pre-existing prescription data can be entered into the system by means of manual typing by the user, reading from the encoded service card during the process of ID validation or obtaining it using Internet connection to a database where such data is stored.

Several other important measurements needed to produce corrective eyewear can be obtained automatically by the eye examination module 19, entered manually or acquired from the database via Internet connection. In addition, a digital camera 23 is co-mounted with the eye examination module 19 to image the person's face, from which the necessary physical measurements can be obtained. Such measurements include bridge size, inter-pupillary distance, temple length, eye size and visual axis. For example, the distance between the temple and the posterior part of the ear is entered as a part of the information for eyeglasses prescription either manually, acquired from the database or measured from the image of the user' head captured by the digital camera 23. In this case multiple images with different views are required and captured by the digital camera either sequentially or simultaneously. In the latter case a second digital camera not shown is provided, which is mounted approximately perpendicular the position of the first digital camera 23. Alternatively, a method for producing measurements necessary to create a custom frame could be performed as described in the U.S. Pat. No. 6,682,195.

Figure 2:
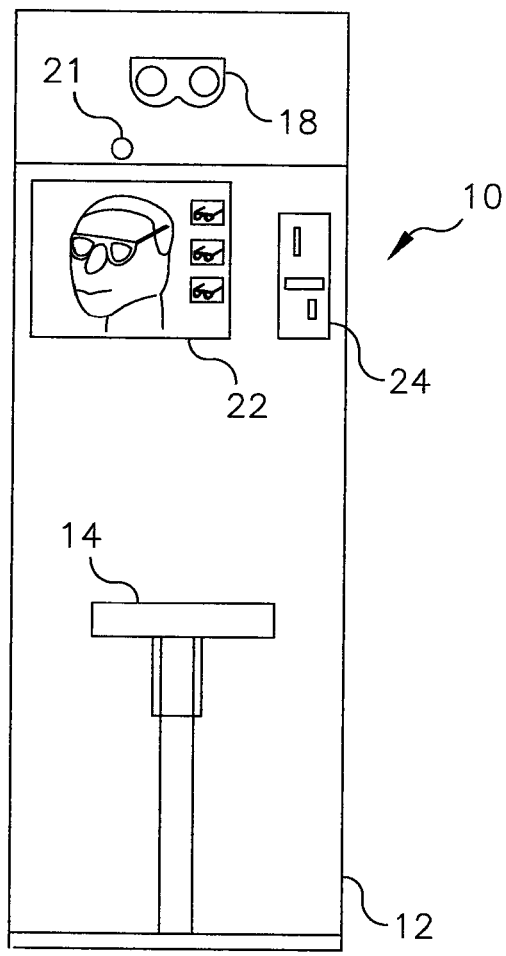
FIG. 2 is a front schematic view of the kiosk of FIG. 1.
Figure 3A:
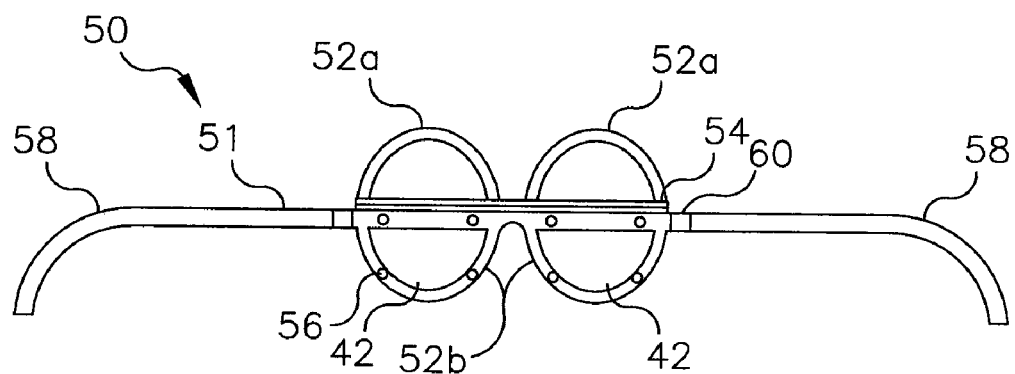
FIGS. 3a and 3b are schematic illustrations of an eyeglass frame useful in the present invention.
Figure 3B:
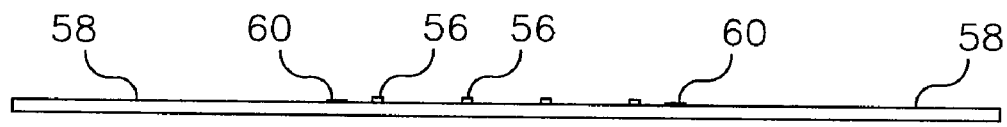
Figure 4:
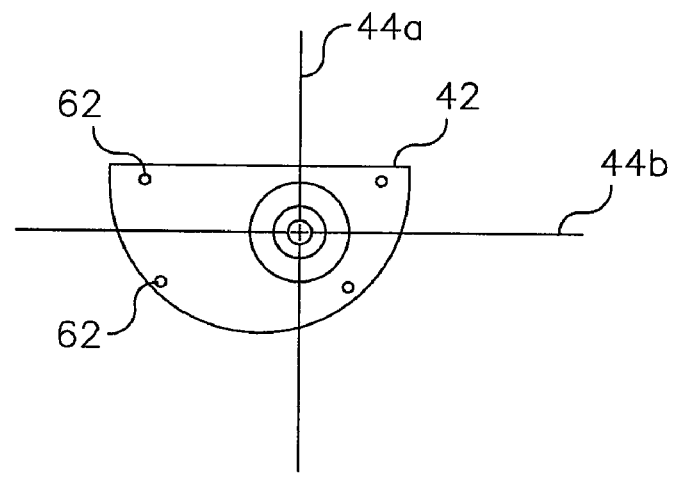
FIG. 4 is a schematic illustration of corrective lenses prior to insertion into the frame of FIGS. 3a and 3b.

The prescription data and physical parameters described above are provided to a fulfillment section 30 for the purpose of fabricating a pair of eyeglasses to correct the vision of the user. In this embodiment, fulfillment section 30 comprises an eyeglass fabrication system 32, which includes, in part, a system process controller 20, a display and user interface device 22, and a payment device 24. A printer 26 is also provided for outputting printed information to the user and producing bill receipts. Further included in fulfillment section 30 are racks of lens supply rolls 34 for providing lenses of varying degrees of refractive correction, a lens cutter 36, frame supply reels 38 and a lens injector 39 that places lenses 42 (FIG. 4) in accordance to the refractive errors or higher order aberration correction information from information processor 17 into the eyeglass frame 50 (FIGS. 3a, 3b) selected from frame supply reels 38. Preferably, the user is able to select a desired frame by means of a touch screen panel on the interactive display of the user interface device 22 as shown in FIG. 2. The parameters of the frame such as the bridge size, the temple length and the inter-pupillary distance are determined based on the measurements of the physical parameters of the user extracted from the user's head and face images or provided by the user. At this time the user is made aware of the cost for each frame option available to him or her and total cost of the eyeglasses. At this point the user may decide not to purchase the eyeglasses and is billed for just the exam and prescription generation. Otherwise the user authorizes a full payment and the eyeglass assembly process is initiated using an appropriately sized frame. The completed eyeglasses are then dispensed into output tray 40 for removal by the user or an attending clerk.

Figure 5:
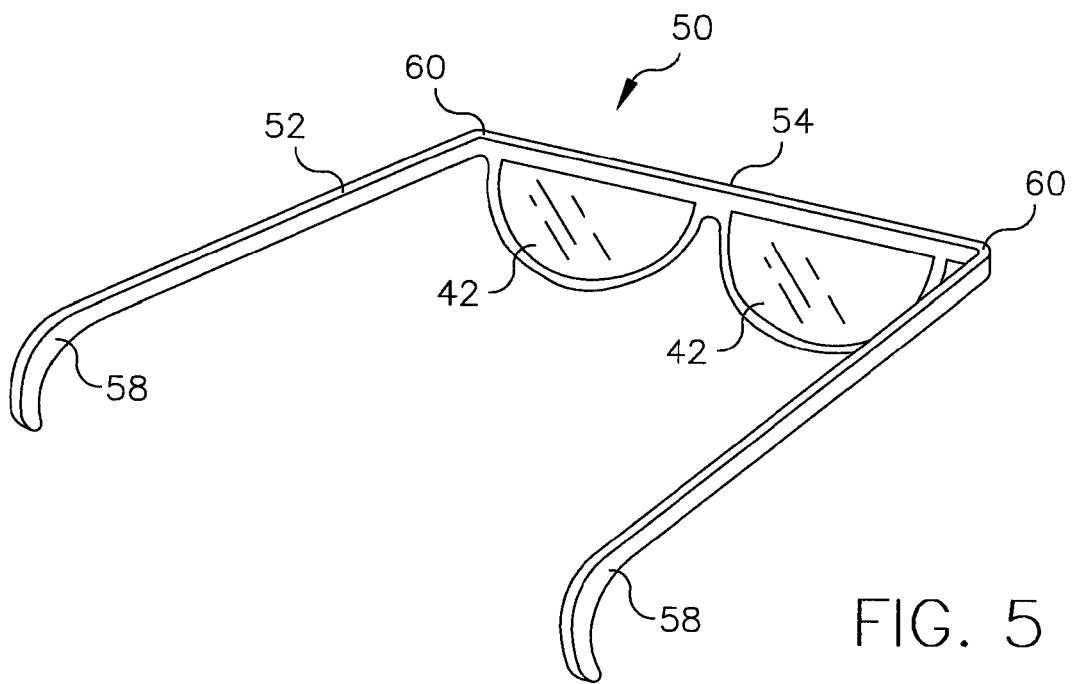
FIG. 5 is a schematic illustration of the eyeglass frame of FIG. 4 with the corrective lenses inserted and the frame adjusted ready for use.

Basic structure for an eyeglass frame 50 useful for the present purpose can be seen with reference to FIGS. 3a, 3b, 4, and 5. As shown, the eyeglass frame 50 comprises a one-piece stamped or molded frame 51 having rims 52a, 52b that are folded together along an integral rim hinge 54 to contain lenses 42 between the rims. An example lens 42 cut by cutter 36 in preparation for insertion into the frame 51 is provided with lens locator holes 62 which have been calculated from the eye examination module test information furnished by either information processor 17 or system process controller 20 for correct placement of the lens centerlines 44a, 44b within the frame rims 52a, 52b. For this purpose, the frame rims are provided with alignment pins 56 for registry with the lens locator holes 62 to assist in aligning the rims during the assembly process. The ear pieces 58 are cut to the appropriate lens and bended based on the measurement of the temple length of the user acquired from the digital camera image, and folded at integral earpiece hinges 60 by the user after removal from tray 40 to thereby complete the assembly as shown in FIG. 5. Alternatively, the earpieces 58 can be a separate piece that is pre-bent and inserted onto the frame 51 automatically, so that the appropriate temple length is obtained.

Figure 6:
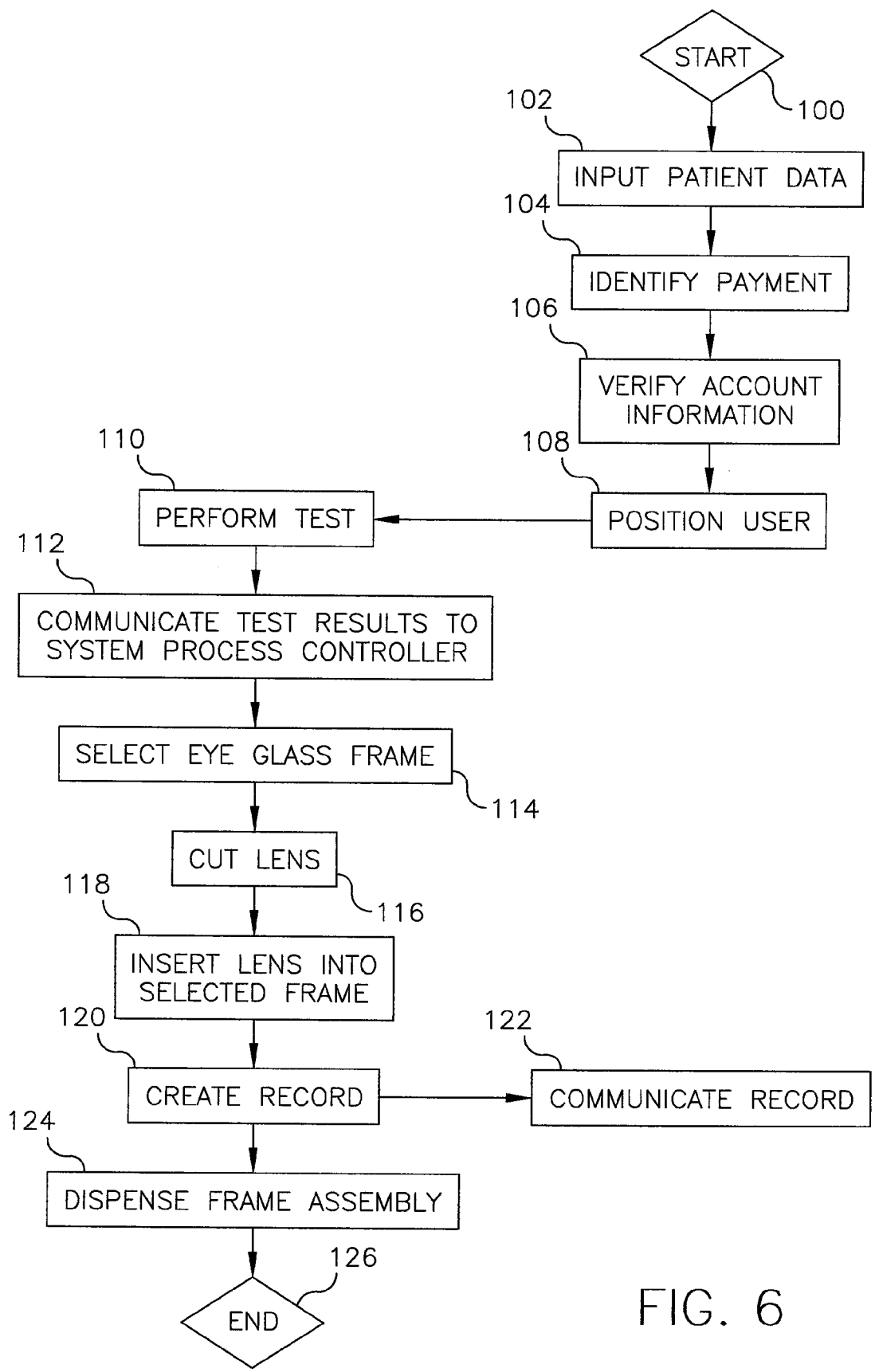
FIG. 6 is a process flow chart of the diagnostic and eyeglass dispensing process employed in the health care kiosk of FIG. 1.

FIG. 6, shows a process flow chart for operation of the eyeglass kiosk of FIG. 1. The process begins by the user pressing the start button (not shown) on the front of the kiosk (step 100). The user, sitting on the seat 14 and facing the display interface device 22 is prompted to enter data such as name, social security number, medical insurance card number, or the like, uniquely identifying the user (step 102). The user is next prompted in step 104 to identify the manner of payment desired, such as for example credit card or insurance card, and, in step 106, the appropriate card is inserted into payment device 24 to obtain the account data utilized later to charge for the services. Alternatively, a verified user ID can be used to access the payment data stored in the system or in a secure server in a different location, which can be accessed via wired or wireless connection. Once the account data is verified, the user is instructed to look into the eyepiece 18 (step 108). The tests are next performed (step 110). In the preferred embodiment the tests include the measurements of refractive errors or higher order aberrations obtained via an operation of the eye examination module 19 and required physical measurements including bridge size, inter-pupillary distance, temple length, eye size and visual axis using digital cameras 23. Alternatively, other diagnostics measurements can be performed at step 110. Once this is done, the prescription for the corrective lenses and necessary measurements for the eyeglasses frame are automatically created as a digital file. At the conclusion of the tests the test data results are communicated via information processor 17 to system process controller 20 for subsequent assembly of the eyeglasses (step 112). The user is next prompted by device to select a desired frame style to proceed (step 114). The user may decide to terminate the process at this time. Once the frame is selected according to the desired style and specified measurements, the proper lenses are cut (step 116) and inserted into the selected frame style of appropriate size (step 118). Subsequently, a data record consisting of the user identity, prescription, cost and payment data is created (step 120), which is then communicated to appropriate output such as printer 26 for a paper record for the user, and, if indicated, via telecommunication to an insurance of a claim for payment of the charges (step 122). At the same time, the completed eyeglasses are dispensed to output tray 40 (step 124), whereupon the process is ended at step 126.

In an alternative form of the test, the user looks through the eyepiece at the display screen where letters or objects of different sizes are successively displayed. The user then reads the letters aloud, and voice recognition software either identifies erroneous reading or confirms a correct reading. In the former case, bigger size letters or figures are displayed until the user correctly identifies the letters or objects. Once the user visual acuity is identified and corrective lens specifications are established, if required, the digital file is then communicated to the system process controller for preparation of the eyeglass fame assembly. Another way of entering the user input can be accomplished via a keyboard. In this case the user would be instructed to type a letter he or she sees on a keyboard.

Figure 7:
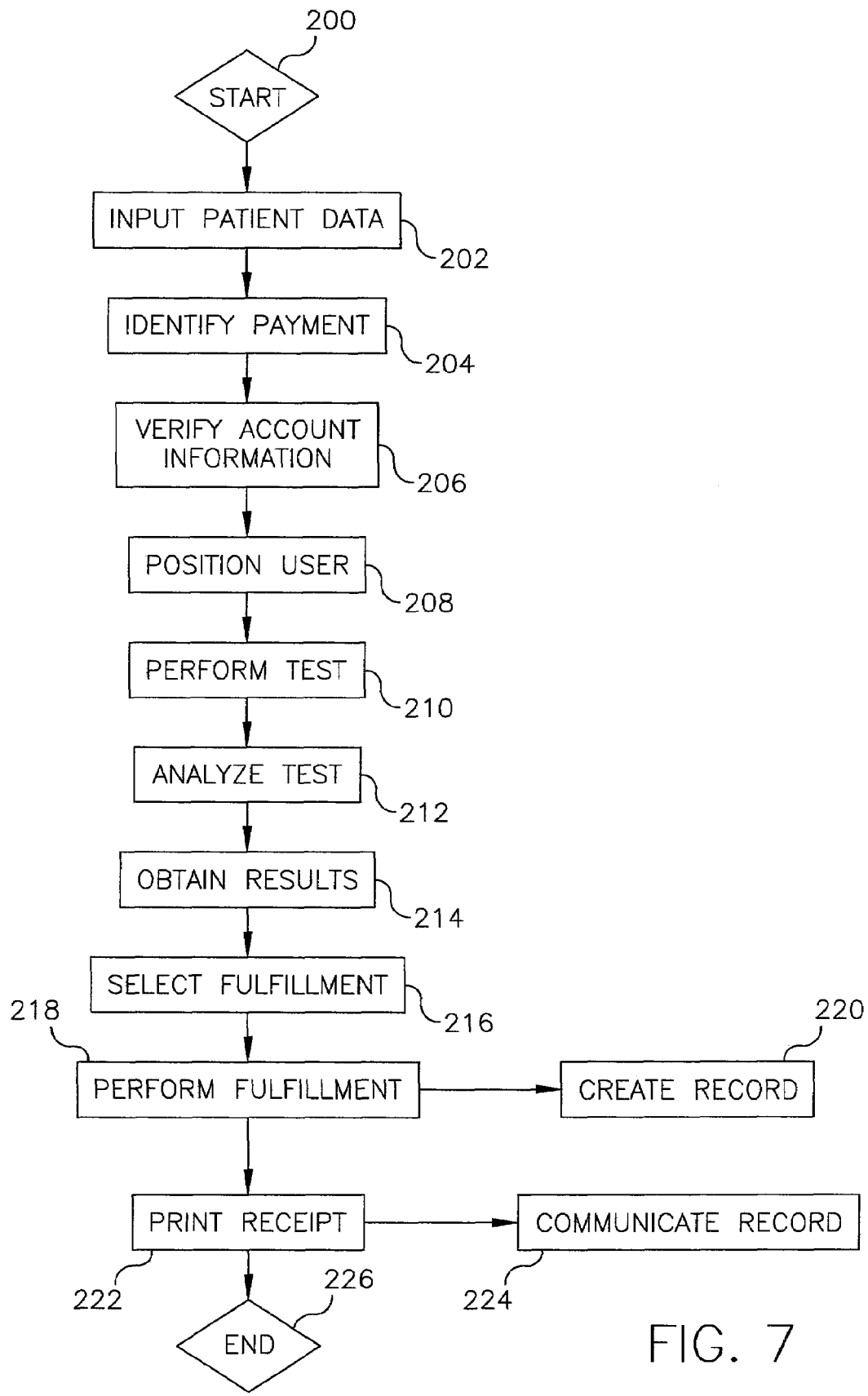
FIG. 7 is a process flow chart for another embodiment of the health care kiosk of the invention used in diagnosing and treating Alzheimer's disease.

Another embodiment of the invention is described in the flow chart of FIG. 7 as an example of diagnosing other health conditions including ophthalmologic diseases, such as cataract, uveitis, glaucoma, macula degeneration, diabetic retinopathy, etc., as well as other diseases such as Alzheimer's disease, mental disorders, diabetes, cancer and drug usage, brain injury, stroke, etc. As a specific example, the flowchart in FIG. 7 will be described using a method of automatic diagnosing and fulfillment of a treatment appropriate for the medical condition found in Alzheimer's disease. In the case of Alzheimer's disease, a treatment may be in the form of memory training.

It has been known that the onset of Alzheimer's disease is suspected when the patient starts experiencing the problems with memorizing new information and forgetting recent information. At present, the memory tests and questionnaires data obtained from the patient and often from family members are used to provide the patient with the diagnosis.

However recent scientific studies have demonstrated that the Alzheimer's Disease (AD) can be detected by inspecting the eye lens using non-invasive optical technology, such as, for example, quasi-elastic light scattering (or dynamic light scattering), or Raman spectroscopy. One method of diagnosing a neuro-degenerative disease such as AD is described in U.S. Patent Application Publication Ser. No. 2002/0091321 A1, in which a dynamic light scattering probe is used to detect and monitor deposition of amyloid protein in the eye which is indicative of a neuro-degenerative disease such as AD. The probe is a portable apparatus consisting of the optical instrument for acquiring the optical information related to the amyloid protein aggregation in the eye lens, connected to the data acquisition and analysis system. Such a probe can be employed in this embodiment of the kiosk as one of the test devices of the eye examination module 19 of the kiosk of FIG. 1.

In FIG. 7, steps 200-206 correspond in operation to steps 100-106 of FIG. 6 described above. In step 208, the user is instructed to position him or herself appropriately for the test. As an example the user is being prompted to look into the eyepiece 18. With the user looking into the eyepiece, the light is generated into the user's eye(s) and the optical probe such as the dynamic light scattering test is performed in step 210 to detect the level of scattering, which is related to the beta amyloid deposition. The quantitative analysis of the amount of scattering is performed in step 212 by comparing the detected user data with a normal group data to indicate the possible presence of neuro-degenerative disease as a result (step 214). Additionally, the data can be compared with the previous data of the same person, which could then be used to monitor the change in the condition evoked by the progression of a disease or a therapeutic intervention In step 216, the appropriate fulfillment for an identified health condition is formulated. One example of such a fulfillment for Alzheimer's disease could be a choice of memory training programs of varying complexity depending on the extent of the condition detected in the previous step. It has been demonstrated in the scientific studies that a memory training exercise such as a face/name association task when performed by Alzheimer's patients, improves their memory (L. Clare et al., "Relearning Face-Name Associations in Early Alzheimer's Disease," Neuropsychology, Vol. 16, No. 4, 2002)

Moreover, it has been shown that the memory enhancement can last for at least several months. Other examples of a fulfillment could be a prescription for the appropriate medication, a CD or a brochure describing the actions the user is instructed to take, or an appointment with the appropriate medical professional, or even dispensing treatment medication In the case where regulations require registered physician authorization for prescription dispensing, patient information and treatment options are automatically sent (via internet, telephone or wirelessly) to the users health care provider or designated physician for approval. The formulated fulfillment is then provided to the user in step 218. As an example, a memory exercise for Alzheimer's disease is given to the user in the form of launching a computer program. Performance of the user during the fulfillment process is then measured, and a record is created, in step 220, documenting the person ID, the optical probe results, and the fulfillment provided. Additionally, the actions of the user, such as for example, performance of the user in the series of memory exercises are recorded and stored for the user and medical professional's subsequent analysis, as well as a new set of baseline information. In the step 222 the payment is withdrawn from the account provide in step 206 and the user obtains a receipt. Additionally, the record created in step 220 can be communicated in step 224 to the medical professional, to the general user file for use as a permanent electronic health record, or other institutions and people upon the user agreement. At the conclusion, step 226 ends the process.

The flowchart shown in FIG. 7 can also be utilized to diagnose and manage a patient's glaucoma or retinal disease. In order to perform this function the eye examination module of FIG. 1 would include an OCT scanning probe such as that described in U.S. Pat. No. 6,293,674. The result of such a probe would be an assessment of presence of glaucoma and retinal disorders. The fulfillment steps 216 and 218 may create a recommendation or an appointment with the ophthalmologist or other relevant medical professional. Alternatively, such a probe could provide a measure of progression of these disorders and assess the efficiency of undergoing treatment.

Figure 8:
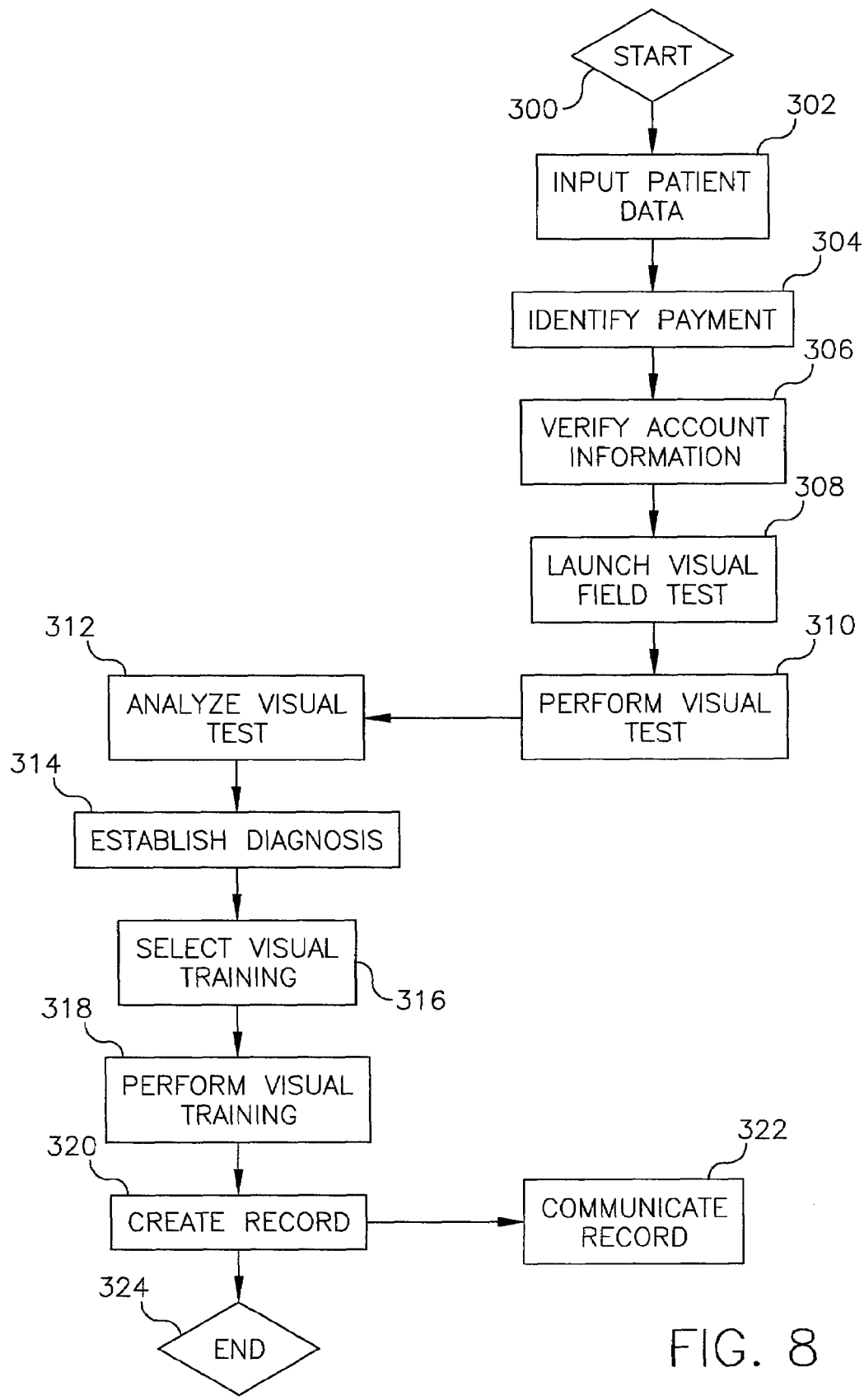
FIG. 8 is a process flow chart for another embodiment of the health care kiosk of the invention used in diagnosing and treating visual field impairment.

The process flow chart of FIG. 8 describes an embodiment of the invention where the eye examination module 19 performs a measurement of the visual field impairment caused by a stroke. An appropriate fulfillment in this case may include providing a therapy in the form of visual training. Recent studies in neuroscience have demonstrated that visual systems possess a remarkable flexibility in adapting to damage and compensating for lost functions. An example of such compensation is described in "Computer-based Training of Stimulus Detection Improves Color and Simple Pattern Recognition in the Defective Field of Hemianopic Subjects," by Kasten et al.; Journal of Cognitive Neuroscience, 12, 2000, pp. 1001-1012. In a randomized placebo-controlled trial, they have demonstrated significant visual field enlargement induced by restitution therapy in patients with cerebral lesions.

FIG. 8 shows a process flow chart illustrating operation of a kiosk for detection of visual field impairment and treatment thereof by visual training according to another embodiment of the present invention. Steps 300-306 are the same as described in the previous embodiments.

In step 308, a visual field test is launched in which the user is prompted to look at the kiosk display to begin a visual field test which is performed in the step 310. An example of a visual test which can be used for this purpose is a computer-based campimetry described in "Computer-based Training of Stimulus Detection Improves Color and Simple Pattern Recognition in the Defective Field of Hemianopic Subjects," by Kasten et al.; Journal of Cognitive Neuroscience, 12, 2000, pp. 1001-1012. Visual field impairment can be investigated by tests for detection of stimuli, shape recognition and color discrimination. The user is instructed to look at a fixation point at the center of the visual field generated by a display or light source throughout the examination and to respond to the visual stimulus by pressing a key on the computer keyboard. The stimuli are shown in different parts of the visual field.

In step 312, quantitative analysis of the reaction time to the presented stimuli is performed. High values of reaction time correspond to high degree of visual impairment. Obtained data are compared with the normal group data to indicate the state of visual impairment and to thereby determine diagnosis (step 314). Additionally, the data can be compared with previous data from the same person, which can then be used to monitor changes in condition over time.

Based on information developed in step 314, suggested fulfillment is formulated and appropriate visual training is selected in step 316. Two examples of the visual training are the Visure and SeeTrain programs described in "Computer-based Training of Stimulus Detection Improves Color and Simple Pattern Recognition in the Defective Field of Hemianopic Subjects," by Kasten et al. Journal of Cognitive Neuroscience, 12, 2000, pp. 1001-1012. Both programs are recommended for people with hemianopic scotoma (diminished vision in half of the visual field).

In step 318, the selected visual training program is performed. For example, the Visure program stimulates systematically the border between intact and deficient zones of the visual field. A large white square that rhythmically changes its size moves from the intact visual field towards the border area. The user is instructed to press a key as long as she/he is able to perceive the stimulus. The square then moves further into the direction of the blind area. If the user is not able to see the stimulus at this position, the stimulus automatically changes the direction of its movement and retracts back into the intact area. The SeeTrain program is based on static stimuli that can be presented stationary. In this case users have to detect the stimulus as quickly as possible and press a response key while the stimulus increased in size or in brightness. By performing this procedure the user exercises his or her visual field and stimulates healing. In step 320, the training results are measured and the performance record is created, documenting the person ID, the diagnosis, and the training performed. Additionally, the performance of the user in the series of training exercises is recorded as well as establishing a new set of baseline information. In step 322, the diagnosis and training results can be communicated to the doctor, to the general user file to used as a permanent electronic health record, or for other institutions and people upon the user agreement. The process then ends in step 324.

Figure 9:
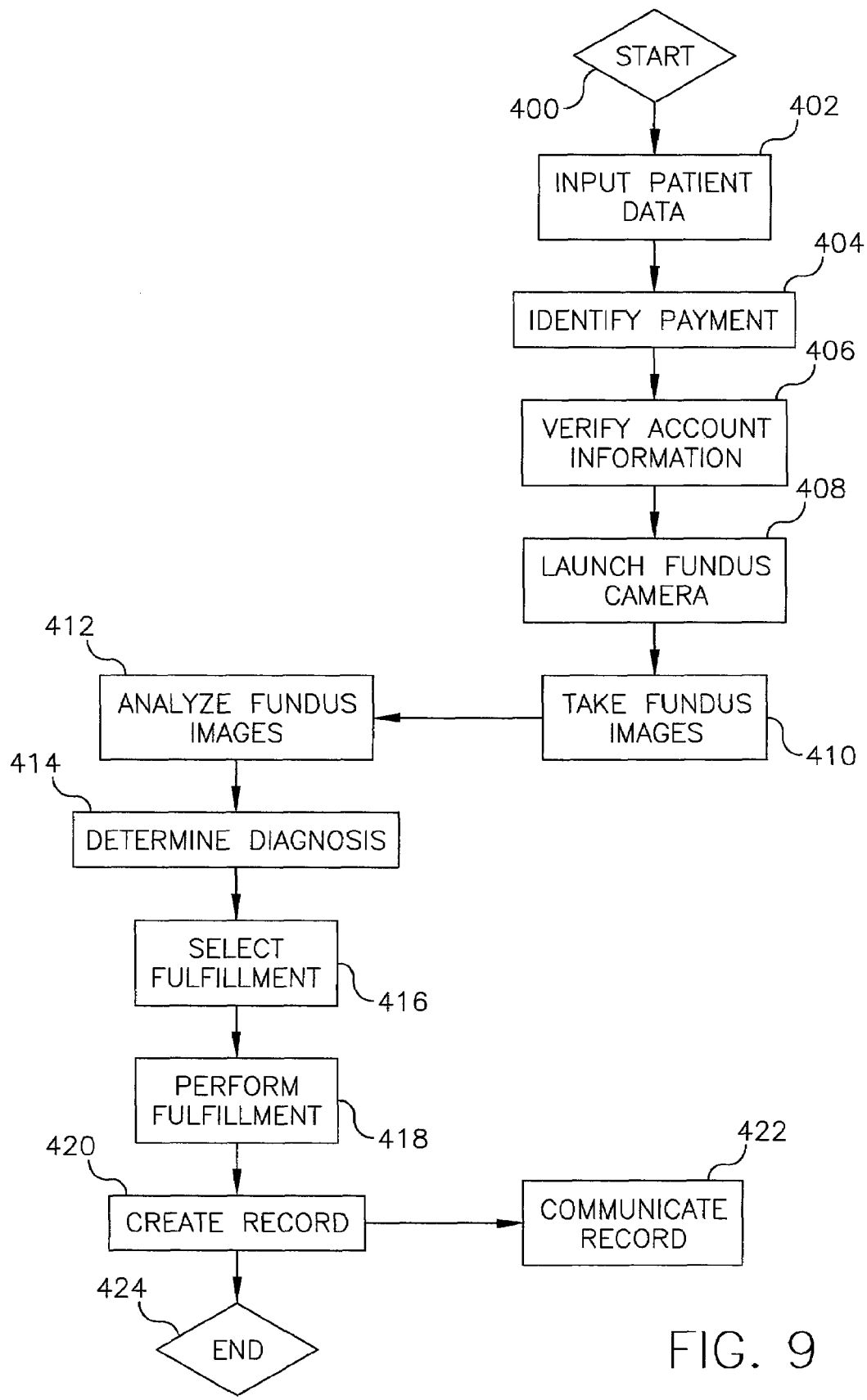
FIG. 9 is a process flow chart for another embodiment of the health care kiosk of the invention used in diagnosing and treating age-related macula degeneration disease (AMD).

The process flow chart of FIG. 9 describes the operation of yet another embodiment of the invention for diagnosing Age-related Macula Degeneration (AMD) based on fundus photography and providing a fulfillment in the form of photodynamic therapy. Photodynamic therapy is a recently developed intervention that uses photosensitive drugs (e.g., verteporfin) and a specially developed low-powered laser to treat AMD patients who still retain some visual acuity. Results of photodynamic therapy using verteporfin have shown it to be safe and effective in randomized clinical trials which have been reported, for example, in "Photodynamic Therapy of Subfoveal Choroidal Neovascularization in Age-related Macular Degeneration With Verteporfin: One-Year Results of 2 Randomized Clinical Trials—TAP Report 1," Treatment of Age-related Macular Degeneration with Photodynamic Therapy (TAP) Study Group., Arch Ophthalmol, Vol. 117, October 1999, pp. 1329-1345.

Referring to FIG. 9, steps 400-406 are the same as described in the previous embodiments. In step 408, the user is prompted to look at a fundus camera, which is a test device for the eye examination module of the kiosk. Fundus camera is a specialized low power microscope with an attached camera, which allows the photographing of the retina (fundus) of the viewer. While the user looks at the camera, flashes of light are generated into the user's eye and retinal images are taken in step 410. The automatic analysis of the retinal images is performed in step 412 and appropriate image parameters are determined (e.g., contrast, lightness homogeneity, etc.). In step 414, the determined images parameters are compared with corresponding parameters for normal group data to indicate the possible presence and type of AMD disease. AMD is classified as either wet (neovascular) or dry (non-neovascular) types. Additionally, the data can be compared with previous data taken from the same person, which can then be used to monitor changes in the condition of the user's retina.

Assuming a diagnosis of AMD, a fulfillment procedure is selected in step 416. In the case of AMD a fulfillment can utilize for example a photodynamic therapy procedure.

Photodynamic therapy is a novel form of treatment for the "wet" or exudative form of age-related macular degeneration. The wet form of macular degeneration involves the growth of abnormal blood vessels called choroidal neovascularization (CNV), beneath the retina resulting in leakage and bleeding. Without treatment, a majority of patients eventually develop scar tissue beneath the macula (the central part of the retina), which results in loss of central vision. In some cases, the blood vessels causing the leakage and bleeding are located outside the central part of vision.

The concept of photodynamic therapy is to selectively close the abnormal blood vessels, eliminating the leakage and bleeding, and stabilizing or improving the vision. This is done without the damaging effect of conventional laser on the normal structures of the retina and back of the eye.

During photodynamic therapy a patient receives an injection of a special dye, for example, Visudyne (liposomal BPD-MA verteporfin) through a vein in the hand or arm. This dye has unique properties which allow it to be used for this treatment. Specifically, this chemical circulates through the body and sticks to the walls of the abnormal blood vessels beneath the macula. At this point in the procedure, a laser is used to shine a light into the back of the eye. The energy produced by this laser is of a very low power and is not damaging like regular laser treatment. Instead, the light simply activates the chemical which is bound to the abnormal blood vessel wall. When the chemical is activated by this light beam, there is closure of the blood vessel. The result is that the fluid and blood which had been leaking beneath the retina is stopped. Over time, the body is able to absorb the blood and fluid, which results in stabilization or improvement in visual function. The blood vessel itself has not been completely destroyed, but rather is no longer leaking nor actively growing.

In spite of the fact that the blood vessel may lie directly beneath the center of vision, photodynamic therapy does not result in damage to the normal retinal tissue or to the wall of the eye. As a result, unlike in traditional laser treatment, vessels directly beneath the center of vision can be effectively treated and closed without causing permanent damage to vision.

After selection of the therapy in step 416, the fulfillment is performed (step 418). For the photodynamic therapy a photosensitive dye (e.g., Visudyne) is administered into user's body and allowed to perfuse the choroidal neovascular membranes (CNVM), which are the leaky vascular structures under the retina in the "wet" form of AMD. Next, a red laser of a specific wavelength (689 nm) is directed into user's eye for few seconds (e.g., 90 seconds). The non-thermal laser light activates the Visudyne producing an active form of oxygen that both coagulates and reduces the growth of abnormal blood vessels. This, in turn, inhibits the leakage of fluid from the CNVM.

In step 420, the record is created, documenting the person ID, the diagnosis, and the procedure performed. In step 422, the diagnosis and treatment descriptions as well as further instructions are communicated to the patient, to the doctor, to the general user file to used as a permanent electronic health record, or for other institutions and people upon user agreement. In the case of photodynamic therapy the instruction to the patient would be to avoid exposure to the sunlight and intense halogen lights for a period of 24 hours until the drug has completely cleared out of the body. This is required since the dye remains within the body for approximately 24 hours. The process then ends in step 424.

The invention has been described in detail with particular reference to certain preferred embodiments thereof, but it will be understood that variations and modifications can be effected within the scope of the invention. For example, rather than a totally enclosed arrangement as described above, the invention encompasses a station comprising separate components interconnected and arranged so as to operate as described without necessarily being contained inside of an enclosure and the term "kiosk" as used herein shall be understood to include such an unenclosed arrangement of individual components.

PARTS LIST

10 kiosk
11 user accommodation section
12 enclosure
13 eye examination and information processing section
14 seat
15 eyes
16 head rest
17 information processor
18 eyepiece
19 eye examination module
20 system process controller
21 ID validation module
22 user interface device
23 camera
24 payment device
26 printer
28 detachable alignment fixture
30 fulfillment section
32 eyeglass fabrication system
34 lens supply rolls
36 lens cutter
38 eyeglass frame supply reels
39 lens injector
40 output tray
42 lens
44*a* lens centerline
44*b* lens centerline
50 eyeglass frame
51 basic frame
52*a* frame rim
52*b* frame rim
54 integral rim hinge
56 alignment pins
58 ear pieces
60 integral earpiece hinges
62 locator holes
100 process starts
102 input patient data
104 identify payment
106 verify account information
108 position user
110 perform test
112 communicate test results to system process controller
114 select eye glass frame
116 cut lens
118 insert lens into selected frame
120 create record
122 communicate record
124 dispense frame assembly
126 process ends
200 process starts
202 input patient data
204 identify payment
206 verify account information
208 position user
210 perform test
212 analyze test
214 obtain results
216 select fulfillment
218 perform fulfillment
220 create record
222 print receipt
224 communicate record
226 process ends
300 process starts
302 input patient data
304 identify payment
306 verify account information
308 launch visual field test
310 perform visual test
312 analyze visual test
314 establish diagnosis
316 select visual training
318 perform visual training
320 create record
322 communicate record
324 process ends
400 process starts
402 input patient data
404 identify payment
406 verify account information
408 launch fundus images
410 take fundus images
412 analyze fundus images
414 determine diagnosis
416 select fulfillment
418 perform fulfillment
420 create record
422 communicate record
424 process ends

The invention claimed is:

1. A health care kiosk adapted to diagnose a medical condition of a user based on an examination of the user's eyes and to provide a remedy therefor, said health care kiosk comprising:
a user accommodation section adapted to locate a user in at least one position that enables an interaction between the station and the user;
a user interface adapted to permit a user to input data relevant to the user;
an eye examination and information processing section adapted to examine at least one of the user's eyes while the user is in said at least one position, wherein said at least one position enables the user to align their eyes with an input to an eye examination module, said eye examination module being adapted to examine the eyes and to provide from the examination at least one of first information relevant to a state of the user's eyes and second, diagnostic, information based on the first information that is indicative of the medical condition of the user; and
a fulfillment section adapted to respond to the information from the examination section to provide a fulfillment remedy pertinent to the state of the eyes or other diagnosed medical condition;
wherein said eye examination module includes an apparatus for examination of the eyes' refraction errors and/or higher order aberrations, said first information comprising prescription data for eyeglasses to correct for the refraction errors and or higher order aberrations indicated by said examination, and wherein the fulfillment section includes equipment responsive to said prescription data for fabrication of eyeglasses that correct the refraction errors and or higher order aberrations.

2. A health care kiosk according to claim 1 wherein said remedy comprises a training program communicated to the user through said user interface.

3. A health care kiosk according to claim 1 wherein said user interface includes a device for making payment for said examination and said fulfillment remedy.

4. A health care kiosk according to claim 1 wherein said user interface includes a device for making payment and said fulfillment section dispenses said fabricated eyeglasses.

5. A health care kiosk according to claim 1 wherein said remedy comprises a fulfillment process for alleviation of the medical condition indicated by said second information.

6. A health care kiosk adapted to diagnose a medical condition of a user based on an examination of the user's eyes and to provide a remedy therefor, said health care kiosk comprising:
a user accommodation section adapted to locate a user in at least one position that enables an interaction between the station and the user;
a user interface adapted to permit a user to input data relevant to the user;
an eye examination and information processing section adapted to examine at least one of the user's eyes while the user is in said at least one position, wherein said at least one position enables the user to align their eyes with an input to an eye examination module, said eye examination module being adapted to examine the eyes and to provide from the examination at least one of first information relevant to a state of the user's eyes and second, diagnostic, information based on the first information that is indicative of the medical condition of the user; and
a fulfillment section adapted to respond to the information from the examination section to provide a fulfillment remedy pertinent to the state of the eyes or other diagnosed medical condition;
wherein said eye examination and information processing section comprises a dynamic light scattering probe with related information processing for determining existence of an Alzheimer's medical condition; and
wherein said remedy comprises a memory enhancement training program communicated to the user through said user interface.

7. A health care kiosk according to claim 1 wherein said eye examination and information processing section comprises an optical coherence tomography probe with related information processing for determining existence of glaucoma or retinal disorders, and or changes of the disease progression.

8. A health care kiosk adapted to diagnose a medical condition of a user based on an examination of the user's eyes and to provide a remedy therefor, said health care kiosk comprising:
a user accommodation section adapted to locate a user in at least one position that enables an interaction between the station and the user;
a user interface adapted to permit a user to input data relevant to the user;
an eye examination and information processing section adapted to examine at least one of the user's eyes while the user is in said at least one position, wherein said at least one position enables the user to align their eyes with an input to an eye examination module, said eye examination module being adapted to examine the eyes and to provide from the examination at least one of first information relevant to a state of the user's eyes and second, diagnostic, information based on the first information that is indicative of the medical condition of the user; and
a fulfillment section adapted to respond to the information from the examination section to provide a fulfillment remedy pertinent to the state of the eyes or other diagnosed medical condition;
wherein said eye examination and information processing section comprises a visual field test device with related information processing for determining existence of a visual field impairment medical condition; and
wherein said remedy comprises a training program that improves color and simple pattern recognition in a defective field of hemianopic subjects communicated to the user through said user interface.

9. A health care kiosk adapted to diagnose a medical condition of a user based on an examination of the user's eyes and to provide a remedy therefor, said health care kiosk comprising:
a user accommodation section adapted to locate a user in at least one position that enables an interaction between the station and the user;
a user interface adapted to permit a user to input data relevant to the user;
an eye examination and information processing section adapted to examine at least one of the user's eyes while the user is in said at least one position, wherein said at least one position enables the user to align their eyes with an input to an eye examination module, said eye examination module being adapted to examine the eyes and to provide from the examination at least one of first information relevant to a state of the user's eyes and second, diagnostic, information based on the first information that is indicative of the medical condition of the user; and
a fulfillment section adapted to respond to the information from the examination section to provide a fulfillment remedy pertinent to the state of the eyes or other diagnosed medical condition;
wherein said eye examination and information processing section comprises fundus camera test device with related information processing for determining existence of age-related macula degeneration; and
wherein said remedy is in the form of photodynamic therapy communicated to the user through said user interface.

10. A health care kiosk according to claim 1 wherein said equipment responsive to said prescription data for fabrication of eyeglasses includes: a supply of lenses of varying degrees of refractive correction; a lens cutter; a supply of eyeglass frames; and a lens injector that places lens in accordance to the refractive errors or higher order aberration correction information into a supplied eyeglass frame.

11. A health care kiosk according to claim 10 wherein said supplied eyeglass frames comprises a one-piece stamped or molded frame having rims that are folded together along an integral rim hinge to contain lenses between the rims.

12. A health care kiosk according to claim 11 wherein a lens cut by said lens cutter in preparation for insertion into an eyeglass frame is provided with lens locator holes, and wherein said eyeglass frame is provided with alignment pins which register with said lens locator holes during assembly of said lens with said eyeglass frame.

* * * * *